(12) United States Patent
Timken et al.

(10) Patent No.: US 7,915,468 B2
(45) Date of Patent: Mar. 29, 2011

(54) ISOMERIZATION OF BUTENE IN THE IONIC LIQUID-CATALYZED ALKYLATION OF LIGHT ISOPARAFFINS AND OLEFINS

(75) Inventors: Hye-Kyung C. Timken, Albany, CA (US); Saleh Elomari, Fairfield, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 117 days.

(21) Appl. No.: 12/418,424

(22) Filed: Apr. 3, 2009

(65) Prior Publication Data

US 2009/0192339 A1 Jul. 30, 2009

Related U.S. Application Data

(63) Continuation of application No. 11/610,782, filed on Dec. 14, 2006, now Pat. No. 7,553,999.

(51) Int. Cl.
*C07C 2/60* (2006.01)
*C07C 2/62* (2006.01)

(52) U.S. Cl. ........ 585/332; 585/331; 585/724; 585/725; 585/727; 585/728; 585/666

(58) Field of Classification Search ................. 585/332, 585/331, 724, 725, 727, 728, 666
See application file for complete search history.

(56) References Cited

U.S. PATENT DOCUMENTS

| | | | |
|---|---|---|---|
| 2,537,283 A | 1/1951 | Schaad | |
| 3,211,801 A | 10/1965 | Holm et al. | |
| 3,270,085 A | 8/1966 | Noddings et al. | |
| 3,304,343 A | 2/1967 | Mitsutani | |
| 3,327,014 A | 6/1967 | Noddings | |
| 3,448,164 A | 6/1969 | Holm et al. | |
| 3,723,564 A | 3/1973 | Tidwell et al. | |
| 3,800,003 A | 3/1974 | Sobel | |
| 3,972,832 A | 8/1976 | Butter et al. | |
| 4,122,245 A | 10/1978 | Nardi et al. | |
| 4,463,071 A | 7/1984 | Gifford et al. | |
| 4,463,072 A | 7/1984 | Gifford et al. | |
| 4,593,146 A | 6/1986 | Johnson et al. | |
| 5,104,840 A | 4/1992 | Chauvin et al. | |
| 5,304,695 A | 4/1994 | Haag et al. | |
| 5,750,455 A | 5/1998 | Chauvin et al. | |
| 6,028,024 A | 2/2000 | Hirschauer et al. | |
| 6,096,680 A | 8/2000 | Park | |
| 6,235,959 B1 | 5/2001 | Hirschauer et al. | |
| 6,797,853 B2 | 9/2004 | Houzvicka et al. | |
| 2003/0060359 A1 | 3/2003 | Olivier-Bourbigou et al. | |
| 2004/0077914 A1 | 4/2004 | Zavilla et al. | |
| 2004/0133056 A1 | 7/2004 | Liu et al. | |
| 2006/0135839 A1 | 6/2006 | Elomari et al. | |

OTHER PUBLICATIONS

Chauvin et al., Alkylation of isobutane with 2-butene using 1-butyl-3-methylimidazolium chloride-aluminium chloride moltene salts as catalysts, Journal of Molecular Catalysis 92, (1994), pp. 155-165, Elsevier Science BV.
Wasserscheid et al., Ionic Liquids in Synthesis, 2003, pp. 275-277, Wiley-Vch Verlag GmbH & Co. KGaA, Welnhein.

*Primary Examiner* — Thuan Dinh Dang
(74) *Attorney, Agent, or Firm* — Susan M. Abernathy; Steven H. Roth

(57) ABSTRACT

A process for producing alkylate comprising contacting a first hydrocarbon stream comprising at least one olefin having from 2 to 6 carbon atoms which contains 1-butene with an isomerization catalyst under conditions favoring the isomerization of 1-butene to 2-butene so the isomerized stream contains a greater concentration of 2-butene than the first hydrocarbon stream and contacting the isomerized stream and a second hydrocarbon stream comprising at least one isoparaffin having from 3 to 6 carbon atoms with an acidic ionic liquid catalyst under alkylation conditions to produce an alkylate stream is disclosed.

12 Claims, No Drawings ns. US 7,915,468 B2

ISOMERIZATION OF BUTENE IN THE IONIC LIQUID-CATALYZED ALKYLATION OF LIGHT ISOPARAFFINS AND OLEFINS

This application is a continuation of U.S. patent application Ser. No. 11/610,782, filed on Dec. 14, 2006; now U.S. Pat. No. 7,553,999 herein incorporated in its entirety.

FIELD OF THE INVENTION

The present invention relates to a process for the alkylation of light isoparaffins with olefins using a catalyst comprising an ionic liquid.

BACKGROUND OF THE INVENTION

In general, conversion of light paraffins and light olefins to more valuable cuts is very lucrative to the refining industries. This has been accomplished by alkylation of paraffins with olefins, and by polymerization of olefins. One of the most widely used processes in this field is the alkylation of isobutane with $C_3$ to $C_5$ olefins to make gasoline cuts with high octane number using sulfuric and hydrofluoric acids. This process has been used by refining industries since the 1940's. The process was driven by the increasing demand for high quality and clean burning high-octane gasoline.

Alkylate gasoline is a high quality and efficient burning gasoline that constitutes about 14% of the gasoline pool. Alkylate gasoline is typically produced by alkylating refineries isobutane with low-end olefins (mainly butenes). Currently, alkylates are produced by using HF and $H_2SO_4$ as catalysts. Although these catalysts have been successfully used to economically produce the best quality alkylates, the need for safer and environmentally friendlier catalysts systems has become an issue to the industries involved.

The quest for an alternative catalytic system to replace the current environmentally unfriendly catalysts has been the subject of varying research groups in both academic and industrial institutions. Unfortunately, thus far, no viable replacement to the current processes has been put into practice at commercial refineries.

Ionic liquids are liquids that are composed entirely of ions. The so-called "low temperature" Ionic liquids are generally organic salts with melting points under 100 degrees C., often even lower than room temperature. Ionic liquids may be suitable for example for use as a catalyst and as a solvent in alkylation and polymerization reactions as well as in dimerization, oligomerization acetylation, metatheses, and copolymerization reactions.

One class of ionic liquids is fused salt compositions, which are molten at low temperature and are useful as catalysts, solvents and electrolytes. Such compositions are mixtures of components which are liquid at temperatures below the individual melting points of the components.

Ionic liquids can be defined as liquids whose make-up is entirely comprised of ions as a combination of cations and anions. The most common ionic liquids are those prepared from organic-based cations and inorganic or organic anions. The most common organic cations are ammonium cations, but phosphonium and sulphonium cations are also frequently used. Ionic liquids of pyridinium and imidazolium are perhaps the most commonly used cations. Anions include, but not limited to, $BF_4^-$, $PF_6^-$, haloaluminates such as $Al_2Cl_7^-$ and $Al_2Br_7^-$, $[(CF_3SO_2)_2N]^-$, alkyl sulphates ($RSO_3^-$), carboxylates ($RCO_2^-$) and many other. The most catalytically interesting ionic liquids for acid catalysis are those derived from ammonium halides and Lewis acids (such as $AlCl_3$, $TiCl_4$, $SnCl_4$, $FeCl_3$ . . . etc). Chloroaluminate ionic liquids are perhaps the most commonly used ionic liquid catalyst systems for acid-catalyzed reactions.

Examples of such low temperature ionic liquids or molten fused salts are the chloroaluminate salts. Alkyl imidazolium or pyridinium chlorides, for example, can be mixed with aluminum trichloride ($AlCl_3$) to form the fused chloroaluminate salts. The use of the fused salts of 1-alkylpyridinium chloride and aluminum trichloride as electrolytes is discussed in U.S. Pat. No. 4,122,245. Other patents which discuss the use of fused salts from aluminum trichloride and alkylimidazolium halides as electrolytes are U.S. Pat. Nos. 4,463,071 and 4,463,072.

U.S. Pat. No. 5,104,840 describes ionic liquids which comprise at least one alkylaluminum dihalide and at least one quaternary ammonium halide and/or at least one quaternary ammonium phosphonium halide; and their uses as solvents in catalytic reactions.

U.S. Pat. No. 6,096,680 describes liquid clathrate compositions useful as reusable aluminum catalysts in Friedel-Crafts reactions. In one embodiment, the liquid clathrate composition is formed from constituents comprising (i) at least one aluminum trihalide, (ii) at least one salt selected from alkali metal halide, alkaline earth metal halide, alkali metal pseudohalide, quaternary ammonium salt, quaternary phosphonium salt, or ternary sulfonium salt, or a mixture of any two or more of the foregoing, and (iii) at least one aromatic hydrocarbon compound.

Other examples of ionic liquids and their methods of preparation may also be found in U.S. Pat. Nos. 5,731,101; 6,797,853 and in U.S. Patent Application Publications 2004/0077914 and 2004/0133056.

In the last decade or so, the emergence of chloroaluminate ionic liquids sparked some interest in $AlCl_3$-catalyzed alkylation in ionic liquids as a possible alternative. For example, the alkylation of isobutane with butenes and ethylene in ionic liquids has been described in U.S. Pat. Nos. 5,750,455; 6,028,024; and 6,235,959 and open literature (*Journal of Molecular Catalysis*, 92 (1994), 155-165; "*Ionic Liquids in Synthesis*", P. Wasserscheid and T. Welton (eds.), Wiley-VCH Verlag, 2003, pp 275).

Aluminum chloride-catalyzed alkylation and polymerization reactions in ionic liquids may prove to be commercially viable processes for the refining industry for making a wide range of products. These products range from alkylate gasoline produced from alkylation of isobutane and isopentane with light olefins, to diesel fuel and lubricating oil produced by alkylation and polymerization reactions.

Light isoparaffins ($iC_3$-$iC_6$) can be alkylated with light olefins ($C_2^=$-$C_5^=$) using acidic ionic liquid catalysts (and in other alkylation processes) to make high octane and clean burning alkylate gasoline. The use of 2-butenes and isobutylene as alkylation olefin feed stocks tend to produce a much higher quality alkylates than 1-butene feed stock. This is due to the nature of the alkylation chemistry with isobutylene and 2-butene which tends to produce the highly desired clean burning alkylates of trimethyl pentanes. Whereas, alkylations with 1-butene tend to produce the less desirable alkylates of dimethyl hexanes.

SUMMARY OF THE INVENTION

The present invention relates to a process for producing alkylate comprising contacting a first hydrocarbon stream comprising at least one olefin having from 2 to 6 carbon atoms which contains 1-butene with an isomerization catalyst under conditions favoring the isomerization of 1-butene to 2-butene so the isomerized stream contains a greater concentration of 2-butene than the first hydrocarbon stream and contacting the isomerized stream and a second hydrocarbon stream comprising at least one isoparaffin having from 3 to 6 carbon atoms with an acidic ionic liquid catalyst under alkylation conditions to produce an alkylate stream.

DETAILED DESCRIPTION

The present invention relates to an alkylation process comprising contacting a hydrocarbon mixture comprising at least one olefin having from 2 to 6 carbon atoms and at least one isoparaffin having from 3 to 6 carbon atoms with an acidic ionic liquid catalyst under alkylation conditions. In accordance with the invention the at least one olefin stream contains 1-butene and at least a portion of the 1-butene is isomerized to 2-butenes before the alkylation reaction.

One component of a feedstock to the process of the present invention is at least one isoparaffin having from 3 to 6 carbon atoms. This component may, for example, be any refinery hydrocarbon stream which contains isoparaffins.

Another component of a feedstock to the process of the present invention is at least one olefin having from 2 to 6 carbon atoms. This component may, for example, be any refinery hydrocarbon stream which contains olefins. Refinery streams containing butenes which may be used as the feed stocks for alkylation typically contain up to 25% 1-butene of the total volume of the olefins in the stream.

The processes according to the present invention are not limited to any specific feedstocks and are generally applicable to the alkylation of $C_3$-$C_6$ isoparaffins with $C_2$-$C_6$ olefins from any source and in any combination.

In accordance with the present invention, at least a portion of the olefin feedstock, which contains 1-butene, is contacted with a catalyst under conditions favoring the isomerization of 1-butene to 2-butene so the isomerized stream contains a greater concentration of 2-butene than in the feed stream. Any isomerization process may be used to achieve this result. As noted above, the conversion or isomerization of 1-butene to 2-butenes makes a better feed stock for an ionic liquid catalyzed alkylation with isobutane and other isoparaffins for making high quality, clean burning and high octane alkylate gasoline.

Significantly, in a sulfuric acid-catalyzed alkylation reaction, 1-butene is isomerized in situ to 2-butene. Therefore, there is no need for isomerization of the olefin-containing feed. Without being bound to any theory, the present invention is based on our observation from the 1-butene alkylation products distribution supporting the notion that, 1-butene does not isomerize in situ in ionic liquid-catalyzed alkylations. So, failing to isomerize 1-butene to 2-butene in the feed to an ionic liquid catalyzed alkylation would produce a lower quality alkylate than would be expected if the mechanism were the same as for the sulfuric acid-catalyzed reaction. Therefore, isomerizing 1-butene to 2-butene in the feed to an ionic liquid catalyzed alkylation in accordance with the present invention produces a higher quality alkylate.

In the alkylation of isobutane with 2-butenes and isobutylene in ionic liquids, for example, the produced alkylates have an octane number that is usually in the high 90s. However, the alkylation of isobutane with 1-butene in ionic liquids leads to alkylates with lower octane numbers of around 70.

Processes for the isomerization of olefinic hydrocarbons are widely known in the art. Many of these use catalysts comprising phosphate. U.S. Pat. No. 2,537,283, for example, teaches an isomerization process using an ammonium phosphate catalyst and discloses examples of butene and pentene isomerization. U.S. Pat. No. 3,211,801 discloses a method of preparing a catalyst comprising precipitated aluminum phosphate within a silica gel network and the use of this catalyst in the isomerization of butene-1 to butene-2. U.S. Pat. Nos. 3,270,085 and 3,327,014 teach an olefin isomerization process using a chromium-nickel phosphate catalyst, effective for isomerizing 1-butene and higher alpha-olefins. U.S. Pat. No. 3,304,343 discloses a process for double-bond transfer based on a catalyst of solid phosphoric acid on silica, and demonstrates effective results in isomerizing 1-butene to 2-butenes. U.S. Pat. No. 3,448,164 teaches skeletal isomerization of olefins to yield branched isomers using a catalyst containing aluminum phosphate and titanium compounds. U.S. Pat. No. 4,593,146 teaches isomerization of an aliphatic olefin, preferably 1-butene, with a catalyst consisting essentially of chromium and amorphous aluminum phosphate.

The art also contains references to the related use of zeolitic molecular sieves. U.S. Pat. No. 3,723,564 teaches the isomerization of 1-butene to 2-butene using a zeolitic molecular sieve. U.S. Pat. No. 3,751,502 discloses the isomerization of mono-olefins based on a catalyst comprising crystalline aluminosilicate in an alumina carrier with platinum-group and Group IV-A metallic components. U.S. Pat. No. 3,800,003 discloses the employment of a zeolite catalyst for butene isomerization. U.S. Pat. No. 3,972,832 teaches the use of a phosphorus-containing zeolite, in which the phosphorus has not been substituted for silicon or aluminum in the framework, for butene conversion.

1-butene is isomerized to the more desirable 2-butenes to achieve the highest possible quality alkylates. This is preferably accomplished in accordance with the present invention using very mild catalytic conditions employing ZSM-5 and other zeolitic-based catalyst. Silica-alumina may be used as an acidic component in the isomerization catalyst, with or without zeolite. Hydrogenating metals may be optionally employed to facilitate the isomerization reaction. Isomerization can be achieved by passing the refinery olefin feed stock containing 1-butene among other olefins over the appropriate catalyst where 1-butene can be easily isomerized to 2-butenes. Terminal olefins do isomerize to internal olefins even in the presence of other internal olefins without any reversible isomerization of the internal olefins (internal-to-terminal).

After isomerization of the olefin-containing stream, a mixture of hydrocarbons as described above is contacted with a catalyst under alkylation conditions. A catalyst in accordance with the present invention comprises at least one acidic halide-based ionic liquid and may optionally include an alkyl halide promoter. The present process is being described and exemplified with reference certain specific ionic liquid catalysts, but such description is not intended to limit the scope of the invention. The processes described may be conducted using any acidic ionic liquid catalysts by those persons having ordinary skill based on the teachings, descriptions and examples included herein.

The specific examples used herein refer to alkylation processes using ionic liquid systems, which are amine-based cationic species mixed with aluminum chloride. In such systems, to obtain the appropriate acidity suitable for the alkylation chemistry, the ionic liquid catalyst is generally prepared to full acidity strength by mixing one molar part of the appropriate ammonium chloride with two molar parts of aluminum chloride. The catalyst exemplified for the alkylation process is a 1-alkyl-pyridinium chloroaluminate, such as 1-butyl-pyridinium heptachloroaluminate.

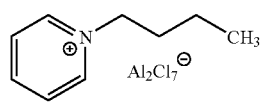

1-Butyl-pyridinium heptachloroaluminate

In general, a strongly acidic ionic liquid is necessary for paraffin alkylation, e.g. isoparaffin alkylation. In that case, aluminum chloride, which is a strong Lewis acid in a combination with a small concentration of a Broensted acid, is a preferred catalyst component in the ionic liquid catalyst scheme.

As noted above, the acidic ionic liquid may be any acidic ionic liquid. In one embodiment, the acidic ionic liquid is a chloroaluminate ionic liquid prepared by mixing aluminum trichloride ($AlCl_3$) and a hydrocarbyl substituted pyridinium halide, a hydrocarbyl substituted imidazolium halide, trialkylammonium hydrohalide or tetraalkylammonium halide of the general formulas A, B, C and D, respectively,

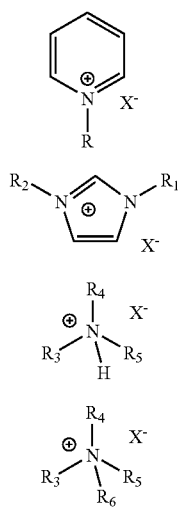

where R=H, methyl, ethyl, propyl, butyl, pentyl or hexyl group and X is a halide and preferably a chloride, and $R_1$ and $R_2$=H, methyl, ethyl, propyl, butyl, pentyl or hexyl group and where $R_1$ and $R_2$ may or may not be the same, and $R_3$, $R_4$, and $R_5$ and $R_6$=methyl, ethyl, propyl, butyl, pentyl or hexyl group and where $R_3$, $R_4$, $R_5$ and $R_6$ may or may not be the same.

The acidic ionic liquid is preferably selected from the group consisting of 1-butyl-4-methyl-pyridinium chloroaluminate, 1-butyl-pyridinium chloroaluminate, 1-butyl-3-methyl-imidazolium chloroaluminate and 1-H-pyridinium chloroaluminate.

In a process according to the invention an alkyl halide may optionally be used as a promoter.

The alkyl halide acts to promote the alkylation by reacting with aluminum chloride to form the prerequisite cation ions in similar fashion to the Friedel-Crafts reactions. The alkyl halides that may be used include alkyl bromides, alkyl chlorides and alkyl iodides. Preferred are isopentyl halides, isobutyl halides, butyl halides, propyl halides and ethyl halides. Alkyl chloride versions of these alkyl halides are preferable when chloroaluminate ionic liquids are used as the catalyst systems. Other alkyl chlorides or halides having from 1 to 8 carbon atoms may be also used. The alkyl halides may be used alone or in combination.

A metal halide may be employed to modify the catalyst activity and selectivity. The metal halides most commonly used as inhibitors/modifiers in aluminum chloride-catalyzed olefin-isoparaffin alkylations include NaCl, LiCl, KCl, $BeCl_2$, $CaCl_2$, $BaCl_2$, $SrCl_2$, $MgCl_2$, $PbCl_2$, CuCl, $ZrCl_4$ and AgCl, as described by Roebuck and Evering (Ind. Eng. Chem. Prod. Res. Develop., Vol. 9, 77, 1970). Preferred metal halides are CuCl, AgCl, $PbCl_2$, LiCl, and $ZrCl_4$.

HCl or any Broensted acid may be employed as co-catalyst to enhance the activity of the catalyst by boasting the overall acidity of the ionic liquid-based catalyst. The use of such co-catalysts and ionic liquid catalysts that are useful in practicing the present invention is disclosed in U.S. Published Patent Application Nos. 2003/0060359 and 2004/0077914. Other co-catalysts that may be used to enhance the activity include IVB metal compounds preferably IVB metal halides such as $ZrCl_4$, $ZrBr_4$, $TiCl_4$, $TiCl_3$, $TiBr_4$, $TiBr_3$, $HfCl_4$, $HfBr_4$ as described by Hirschauer et al. in U.S. Pat. No. 6,028,024.

Due to the low solubility of hydrocarbons in ionic liquids, olefins-isoparaffins alkylation, like most reactions in ionic liquids is generally biphasic and takes place at the interface in the liquid state. The catalytic alkylation reaction is generally carried out in a liquid hydrocarbon phase, in a batch system, a semi-batch system or a continuous system using one reaction stage as is usual for aliphatic alkylation. The isoparaffin and olefin can be introduced separately or as a mixture. The molar ratio between the isoparaffin and the olefin is in the range 1 to 100, for example, advantageously in the range 2 to 50, preferably in the range 2 to 20. In a semi-batch system the isoparaffin is introduced first then the olefin, or a mixture of isoparaffin and olefin. Catalyst volume in the reactor is in the range of 2 vol % to 70 vol %, preferably in the range of 5 vol % to 50 vol %. Vigorous stirring is desirable to ensure good contact between the reactants and the catalyst. The reaction temperature can be in the range −40° C. to +150° C., preferably in the range −20° C. to +100° C. The pressure can be in the range from atmospheric pressure to 8000 kPa, preferably sufficient to keep the reactants in the liquid phase. Residence time of reactants in the vessel is in the range a few seconds to hours, preferably 0.5 min to 60 min. The heat generated by the reaction can be eliminated using any of the means known to the skilled person. At the reactor outlet, the hydrocarbon phase is separated from the ionic phase by decanting, then the hydrocarbons are separated by distillation and the starting isoparaffin which has not been converted is recycled to the reactor.

Typical alkylation conditions may include a catalyst volume in the reactor of from 5 vol % to 50 vol %, a temperature of from −10° C. to +100° C., a pressure of from 300 kPa to 2500 kPa, an isopentane to olefin molar ratio of from 2 to 8 and a residence time of 5 min to 1 hour.

In one embodiment of a process according to the present invention, high quality gasoline blending components of low volatility are recovered from the alkylation zone. Those blending components are then preferably blended into gasoline.

The following Examples are illustrative of the present invention, but are not intended to limit the invention in any way beyond what is contained in the claims which follow.

EXAMPLES

Example 1

Continuous Alkylation of Isobutane with C4 Olefin Isomers

Each isomer of the four butene isomers was alkylated with isobutane in a 100 cc continuously stirred tank reactor. An 8:1 molar ratio of isobutane and butene mixture was fed to the reactor while vigorously stirring at 1600 RPM. An ionic liquid catalyst, N-butylpyridinium chloroaluminate, was fed to the reactor via a second inlet port targeting to occupy ~10 vol % in the reactor. A small amount of anhydrous HCl gas was added to the process. The average residence time for the combined volume of feeds and catalyst was about 8-20 min. The outlet pressure was maintained at 100 psig using a back-pressure regulator. The reactor temperature was maintained at about 0-20° C. The reactor effluent was separated in a 3-phase separator into C4-gas; alkylate hydrocarbon phase, and the ionic liquid catalyst. The total liquid product and gas samples were analyzed using gas chromatography (GC). Research octane number of alkylate gasoline was calculated based on GC composition of C5+ fraction using research octane number of pure compounds assuming volumetric linear blending.

The effect of C4 olefin isomer to the research octane number of the alkylate gasoline is tremendous as shown in Table 1.

TABLE 1

Effect of C4 Olefin on Alkylate Gasoline Octane Number

| Feed Olefin Source | cis-2-butene | trans-2-butene | isobutylene | 1-butene |
|---|---|---|---|---|
| C5+ gasoline Research Octane Number | 98.6 | 98.4 | 92.9 | 66.3 |
| C8 Composition | | | | |
| % tri-Me-pentane/total C8 | 95.3 | 95.3 | 84.2 | 4.4 |
| % Di-Me-hexane/total C8 | 4.5 | 4.5 | 14.4 | 85.1 |
| % Me-Heptane/total C8 | 0.2 | 0.2 | 1.3 | 10.4 |
| % n-Octane/total C8 | 0.0 | 0.0 | 0.0 | 0.0 |
| Sum | 100.0 | 100.0 | 100.0 | 100.0 |

With 2-butene and isobutylene, the present process will produce product with higher Research Octane Numbers of 98-99 and 93. The main C8 product from 2-butenes and isobutylene alkylation is trimethylpentanes which have excellent octane numbers. However, with 1-butene the alkylate gasoline Research Octane Number is only 66. The main C8 product from 1-butene alkylation is dimethylhexanes which have poor octane numbers. By converting 1-butene to 2-butene, the Octane Number of the alkylate gasoline produced by the present invention is substantially improved.

Example 2

To a 30 gm of H-ZSM-5/Al2O5 in 300 cc autoclave 100 gm of liquefied 1-butene (99% purity) was added. The mixture was heated to 100° C. and stirred at the autogenic pressure (435 psi) for 1 hour. A gas samples before and after the reaction were analyzed by GC analysis. The GC analysis indicated that the sample collected after the reaction contained 79% 2-butenes and 21% 1-butene.

By combining this olefin isomerization process with the alkylation process using the ionic liquid catalyst, the Research Octane Number of the final alkylate gasoline is increased by 25 numbers.

Example 3

The reaction procedure described in Example 2 was repeated exactly with the exception of using 100 gm of 50/50 mixture of 1-butene and 2-butene instead of 1-butene, GC analysis of a gas sample after the reaction indicated that mixture now contains 84:16 mixture of 2-butene:1-butene. This indicates 68% conversion of 1-butene to 2-butenes.

By combining this olefin isomerization process with the alkylation process using the ionic liquid catalyst, the Research Octane Number of the final alkylate gasoline is increased by 9 numbers.

Example 4

The reaction described in Example 2 was repeated with the exception of using 100 gm of a refinery feed mixture containing 55% light paraffins and 45% light olefins. The olefin portion contained 25% 1-butene among other olefins including 2-butenes, propylene and small amounts of others (1-butene is ~11% of the total volume in the feed based on GC analysis before the reaction). GC analysis of a gas sample after the reaction showed the presence of only 4% 1-butene in the gas mixture indicating a 62% conversion to 2-butenes.

By combining this olefin isomerization process with the alkylation process using the ionic liquid catalyst, the Research Octane Number of the final alkylate gasoline is increased by 5 numbers.

There are numerous variations on the present invention which are possible in light of the teachings and supporting examples described herein. It is therefore understood that within the scope of the following claims, the invention may be practiced otherwise than as specifically described or exemplified herein.

What is claimed is:

1. A process for producing alkylate comprising contacting a first hydrocarbon stream consisting essentially of 1-butene with an isomerization catalyst comprising a ZSM-5 zeolite under conditions favoring the isomerization of 1-butene to 2-butene to produce an isomerized stream containing at least 80% of 2-butene and contacting the isomerized stream and a second hydrocarbon stream comprising at least one isoparaffin having from 3 to 6 carbon atoms with an acidic ionic liquid catalyst under alkylation conditions to produce an alkylate stream.

2. In an alkylation process in which an isomerized stream containing at least 80% of 2-butene and at least one isoparaffin having from 3 to 6 carbon atoms are contacted in an alkylation zone under alkylation conditions with a catalyst comprising an acidic ionic liquid to produce an alkylate stream, the improvement comprising contacting an olefinic feed consisting essentially of 1-butene with an isomerization catalyst comprising a ZSM-5 zeolite under conditions favoring the isomerization of 1-butene to 2-butene to produce the isomerized stream containing at least 80% of 2-butene.

3. A process for producing alkylate comprising contacting a first hydrocarbon stream consisting essentially of 1-butene with an isomerization catalyst comprising a ZSM-5 zeolite under conditions favoring the isomerization of 1-butene to 2-butene to produce an isomerized stream containing at least 80% of 2-butene and contacting the isomerized stream and a second hydrocarbon stream comprising at least one isoparaffin having from 3 to 6 carbon atoms with an acidic ionic liquid catalyst under alkylation conditions to produce an alkylate stream having a RON of at least 93.

4. In an alkylation process in which an isomerized stream containing at least 80% of 2-butene and at least one isoparaffin having from 3 to 6 carbon atoms are contacted in an alkylation zone under alkylation conditions with a catalyst comprising an acidic ionic liquid to produce an alkylate stream having a RON of at least 93, the improvement comprising contacting an olefinic feed consisting essentially of 1-butene with an isomerization catalyst comprising a ZSM-5 zeolite under conditions favoring the isomerization of 1-butene to 2-butene to produce the isomerized stream containing at least 80% 2-butene.

5. The process according to claim 1, claim 2, claim 3, or claim 4, where the acidic ionic liquid is a chloroaluminate ionic liquid of the general formulas A, B, C and D, respectively,

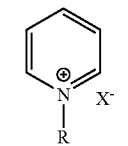

A

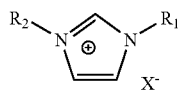

B

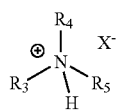

C

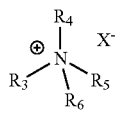

D where R=H, methyl, ethyl, propyl, butyl, pentyl or hexyl group and X is a halide and preferably a chloride, and $R_1$ and $R_2$=H, methyl, ethyl, propyl, butyl, pentyl or hexyl group and where $R_1$ and $R_2$ may or may not be the same, and $R_3$, $R_4$, and $R_5$ and $R_6$=methyl, ethyl, propyl, butyl, pentyl or hexyl group and where $R_3$, $R_4$, $R_5$ and $R_6$ may or may not be the same.

6. The process according to claim 5, wherein the acidic ionic liquid is selected from the group consisting of 1-butyl-4-methyl-pyridinium chloroaluminate (BMP), 1-butyl-pyridinium chloroaluminate (BP), 1-butyl-3-methyl-imidazolium chloroaluminate BMIM) and 1-H-pyridinium chloroaluminate (HP).

7. The process according to claim 1, claim 2, claim 3, or claim 4, wherein the isoparaffin is selected from the group consisting of isobutane, isopentane, and mixtures thereof.

8. The process according to claim 1, or claim 3, wherein the alkylation conditions include a catalyst volume in the reactor of from 5 vol % to 50 vol %, a temperature of from −10° C. to 100° C., a pressure of from 300 kPA to 2500 kPa, an isopentane to olefin molar ratio of from 2 to 8 and a residence time of 1 minute to 1 hour.

9. The process according to claim 1, or claim 3, wherein the acidic ionic liquid catalyst further comprises an alkyl halide.

10. The process according to claim 9, where the alkyl halide is selected from the group consisting of methyl halide, ethyl halide, propyl halide, 1-butyl halide, 2-butyl halide, tertiary butyl halide, pentyl halides, iospentyl halide, hexyl halides, isohexyl halides, heptyl halides, isoheptyl halides, octyl halides and isooctyl halides.

11. The process of claim 1, or claim 3, wherein the alkylate stream has 0.0 wt % n-octane.

12. The process of claim 1, or claim 3, wherein the alkylate stream has a RON that is increased from 5 to 32 numbers compared to a comparison alkylate stream made from the first hydrocarbon stream without the step of contacting with the isomerization catalyst.

* * * * *